(12) United States Patent
Lee

(10) Patent No.: US 6,228,114 B1
(45) Date of Patent: May 8, 2001

(54) ADJUSTABLE CORNEAL RING

(76) Inventor: Joseph Y. Lee, 11435 Via Lido, Loma Linda, CA (US) 92354

( * ) Notice: Subject to any disclaimer, the term of this patent is extended or adjusted under 35 U.S.C. 154(b) by 6 days.

(21) Appl. No.: 08/971,324

(22) Filed: Nov. 17, 1997

Related U.S. Application Data

(63) Continuation-in-part of application No. 08/829,846, filed on Apr. 1, 1997, now Pat. No. 5,855,604.

(51) Int. Cl.⁷ ........................................... A61F 2/14
(52) U.S. Cl. ............................................. 623/5.12
(58) Field of Search .............. 623/5, 5.11, 5.12; 606/166, 167

(56) References Cited

U.S. PATENT DOCUMENTS

| | | |
|---|---|---|
| 4,298,004 | 11/1981 | Schachar et al. . |
| 4,452,235 | 6/1984 | Reynolds . |
| 4,607,617 | 8/1986 | Choyce . |
| 4,624,669 | 11/1986 | Grendahl . |
| 4,655,774 | 4/1987 | Choyce . |
| 4,688,570 | 8/1987 | Kramer et al. . |
| 4,815,463 | 3/1989 | Hanna . |
| 4,834,750 | 5/1989 | Gupta . |
| 4,941,093 | 7/1990 | Marshall . |
| 4,961,744 | 10/1990 | Kilmer et al. . |
| 4,976,719 | 12/1990 | Siepser . |
| 5,090,955 | 2/1992 | Simon . |
| 5,123,921 | 6/1992 | Werblin et al. . |
| 5,188,125 | 2/1993 | Kilmer et al. . |
| 5,236,970 | 8/1993 | Christ et al. . |
| 5,300,118 | 4/1994 | Silvestrini et al. . |
| 5,312,424 | 5/1994 | Kilmer et al. . |
| 5,318,047 | 6/1994 | Davenport et al. . |
| 5,331,073 | 7/1994 | Weinschenk, III et al. . |
| 5,372,580 | 12/1994 | Simon et al. . |
| 5,391,201 | 2/1995 | Barrett et al. . |
| 5,405,384 | 4/1995 | Silvestrini . |
| 5,466,260 | 11/1995 | Silvestrini et al. . |
| 5,480,950 | 1/1996 | Wang et al. . |
| 5,505,722 | 4/1996 | Kilmer et al. . |
| 5,547,468 | 8/1996 | Simon et al. . |
| 5,607,437 | 3/1997 | Simon et al. . |
| 5,693,092 | * 12/1997 | Silvestrini et al. ................ 623/5 |
| 5,733,334 | * 3/1998 | Lee ................................ 623/5 |

FOREIGN PATENT DOCUMENTS 388746   7/1993  (RU) .

OTHER PUBLICATIONS

McCarey, B. et al., "Refractive Keratoplasty with Intrastromal Hydrogel Ienticular Implants," Assoc. For Res. In Vis. And Ophthal., Inc., vol. 21, No. 1, Part 1, Jul. 1981, pp. 107–115.

Beekhuis, W.H. et al., "Hydration Stability of Intracorneal Hydrogel Implants," Investigative Ophthamology & Visual Science, vol. 26, Nov. 1985, pp. 1634–1636.

Beekhuis, W.H. et al., "Hydrogel Keratophakia: A Microkeratone Dissection in the Monkey Model," British Journal of Ophthamology, 1986, pp. 192–198.

(List continued on next page.)

Primary Examiner—David J. Isabella
(74) Attorney, Agent, or Firm—McCutchen, Doyle, Brown & Enersen, LLP

(57) ABSTRACT

An apparatus for adjusting the corneal curvature of the eye comprising a corneal implant having an elongated, hollow tubular shell which is implantable into the cornea in encircling relation to the central optic zone of the cornea. The implant has hinged portions along its the inner and outer arcs, and the corneal implant is filled with a predetermined amount of a biocompatible material in various forms such as rings or strands. The biocompatible material is strategically located within the flexible shell to alter its dimensions in thickness or diameter and thereby adjust the corneal curvature to correct refractive error.

18 Claims, 9 Drawing Sheets

OTHER PUBLICATIONS

McCarey, B. et al., "Refractive Keratoplasty in Monkeys Using Intracorneal Lenses of Various Refractive Indexes," Arch Ophthamol, vol. 105, Jan. 1987, pp. 123–126.

Beekhuis, W.H. et al., "Complications of Hydrogel Intracorneal Lenses in Monkeys," Arch Ophthalmol, vol. 105, Jan. 1987, pp. 116–122.

Fleming, J. et al., "The Intrastromal Corneal Ring: Two Cases in Rabbits," Journal of Refractive Surgery, vol. 3, No. 6, Nov./Dec. 1987, pp. 227–232.

Climenhaga, H. et al., "Effect of Diameter and Depth on the Response to Solid Polysulfone Intracorneal Lenses in Cats," Arch Ophthamol, vol. 106, Jun. 1988, pp. 818–824.

Burris, T. et al., "Effects of Intrastromal Corneal Ring Size and Thickness on Corneal Flattening in Human Eye," Refractive & Corneal Surgery, vol. 7, Jan./Feb. 1991, pp. 46–50.

Simon, G. et al., "Refractive Remodeling of the Cornea by Intrastromal Rings," Abstracts, Eighth International Congress of Eye Research, The International Society of Eye Research, Sep. 1988.

Burris, T. et al., "Flattening of Central Corneal Curvature with Intrastromal Corneal Rings of Increasing Thickness: An Eye–Bank Eye Study," J Cataract Refract. Surg., vol. 19, 1993, pp. 182–187.

Elander, R. et al., "Principles and Practice of Refractive Surgery," W.B. Saunders Company, including Chap. 21, *Alloplastic Materials in Lamellar Surgery*, by McCarey, Chap. 39, *Synthetic Epikeratoplasty*, by Thompson et al., Chap. 40, *Intrastromal Corneal Ring*, by Schanzlin et al., 1997.

Azar, D., "Refractive Surgery," Appleton & Lange, including Chap. 15, *Corneal Biomechanics in Refractive Surgery*, by Hjortdal, Chap. 27, *The Intrastromal Corneal Ring for the Correction of Myopia*, by Verity et al., Chap. 28, *Intracorneal Alloplastic Inclusions*, by Khoury et al., 1997.

Barraquer, J., "Basis of Refractive Keratoplasty," Refractive & Corneal Surgery, vol. 5, May/Jun. 1989, pp. 179–193.

Blavatskaia, E.D., "The Use of Intralamellar Homoplasty in Order to Reduce Refraction of the Eye," Arch. Soc. Ophthalmol. Optom., vol. 6, 1988.

Harr, D., "KeraVision Begins Implanting Corneal Reshaping Device in Blind Eyes," Refractive & Corneal Surgery, vol. 7, Sep./Oct. 1991, p. 343.

Hartmann et al., "Intrastromal Implantation of an Adjustable Plastic Ring to Alter the Corneal Refraction," University Eye Clinic, Cologne.

Simon, G. et al., "Gel Injection Adjustable Keratoplasty," Graefe's Arch Clin Exp. Ophthalmol, 1991, pp. 418–425.

Simon, G. et al., "Modification, Calibration, and Comparative Testing of an Automated Surgical Keratometer," Refractive & Corneal Surgery, vol., Mar./Apr. 1991, pp. 151–160.

Thompson, K. et al., "Emerging Technologies for Refractive Surgery: Laser Adjustable Synthetic Epikeratoplasty," Refractive & Corneal Surgery, vol. 5, Jan./Feb. 1989, pp. 46–48.

Thompson, K., "Will the Excimer Laser Resolve the Unsolved Problems with Refractive Surgery?", Refractive & Corneal Surgery, vol. 6, Sep./Oct. 1990, pp. 315–317.

* cited by examiner

ADJUSTABLE CORNEAL RING

CROSS-REFERENCE TO RELATED APPLICATIONS

This application is a continuation-in-part of U.S. patent application No. 08/829,846, filed Apr. 1, 1997 now U.S. Pat. No. 5,855,604.

BACKGROUND OF THE INVENTION

This invention relates to a method and apparatus for adjusting corneal curvature and, more particularly, to an implantable device adapted for insertion into the peripheral cornea of an eye and which may be modified in the amount of corneal volume it displaces at the time of insertion and at post-operative times to correct refractive error by adjusting or removing solid material from the implanted device or augmenting said device with solid material.

Ametropia, an undesirable refractive condition of the eye, has three main subdivisions: myopia, hyperopia, and astigmatism. In myopia, by far the most common type of ametropia, the parallel light rays 1 which enter the eye as shown in FIG. 1 come to a focus F1 in front of the retina 2 as shown in FIG. 2. In hyperopia, the rays of light 1 come to a focus F2 behind the retina 2 as shown in FIG. 3. When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye which acts to change the light-bending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomileusis which can steepen or flatten the central cornea. Keratomileusis was introduced by Barraquer of Colombia in 1961 and essentially involves grinding a corneal button into an appropriate shape to correct the refractive error and replacing the reshaped corneal button. Some of the more common keratorefractive procedures are discussed below, none of which have currently shown itself to have all the characteristics of an ideal keratorefractive procedure. The disadvantages of corneal refractive surgery include limited predictability, lack of reversibility, corneal destabilization, optical zone fibrosis, post-operative discomfort, and visual symptoms such as glare, halos, and starbursts.

The goal of the ideal keratorefractive procedure is to allow all the advantages of eyeglasses or contact lenses, namely, being able to correct a wide range of refractive errors, accuracy or predictability, to allow reversibility in the event that the refractive state of the eye changes and it becomes necessary to adjust the correction again, to yield minimal complications and be associated with technical simplicity, low cost, and being aesthetically acceptable to the patient.

For well over a century, ophthalmologists have searched for a surgical method to permanently correct refractive errors. At least 15 different techniques have been developed and considerable experience accumulated in both animal and human models. Laser photorefractive keratotomy has come the closest to gaining widespread acceptance in our profession but the difficulty in gaining acceptance for keratorefractive procedures are because of the unsolved problems with poorly predictable and unstable refractive outcomes, adverse effects on the quality of vision, lack of adjustability, and irreversibility.

Poor predictability looms as the largest unsolved problem with refractive corneal surgery. The two major factors that contribute to poor predictability are: (1) the variability and inaccuracy inherent with manual surgical techniques, and (2) the variable influence of corneal wound healing in determining the refractive outcome. Until these two deficiencies are corrected, it is unlikely that a refractive surgical procedure will predictably correct ametropia to within a half diopter, the margin which can be achieved routinely with glasses or contact lenses. Photorefractive Keratectomy (PRK) offers the possibility of solving one of the major causes of poor predictability by reducing the surgical variability of the procedure. A major unresolved issue is how the second nemesis that causes poor predictability, corneal wound healing, will affect the results of PRK.

Reasons for a lack of perfectly predictable outcomes in any keratorefractive procedure, in a particular individual patient, include variations in individual surgical technique, the difficulty in repetitively performing manual microsurgery to submicrosurgical tolerances, and idiosyncracies of individual patients' wound healing.

In radial keratotomy (RK) multiple peripheral radially directed incisions are made into the cornea at 90–95% depth in an attempt to flatten the central cornea and thus correct myopia. The problem of unpredictability of result was tackled by multiple extensive retrospective analyses of the patients in whom surgery had already been performed. These studies revealed certain factors that seemed to control the outcome of the surgery, such as the size of the optical zone, the initial keratometric readings, corneal diameter, corneal rigidity, number of incisions, incision depth, intraocular pressure, thickness of the cornea, and degree of astigmatism. Age and sex are also factors that are taken into consideration in most of the nomograms which have been devised to predict what effect to expect for a certain surgery. At one point, many experts in the field considered it nearly impossible to fully and accurately correct patients in one surgery and felt that RK should be considered a two-stage surgery, with the initial surgery to achieve the "ball-park" correction, followed by an enhancement procedure to adjust or titrate the result near the desired outcome for an individual eye. It was felt that because of individual variability which may lead to an under or over-correction in the individual different from that predicted by the nomogram, attempting to fully correct the refractive error in one surgery could lead to over-correction in a not insignificant percent of the surgeries, resulting in hyperopia which is much more difficult to correct. Unfortunately, the second-stage surgery is even less predictable than the initial procedure. No one has yet devised a formula to take into account the profound changes which occur in the cornea after the initial RK, especially when weeks or months have passed. Most studies quote only 50–60% of eyes achieving 20/20 or better visual acuity following RK. Patients who are accustomed to 20/20 or better corrected visual acuity before surgery are not typically satisfied with less than 20/25 or 20/30 uncorrected post-operative visual acuity.

In addition, a gradual hyperopic shift is a major concern after RK. Refractive stability is critical for all refractive procedures but all corneal refractive procedures show significant degrees of instability. To date, there have been no clear explanation of why the cornea is destabilized by RK. A recent report on the long-term results of RK stressed the "natural" hyperopic refractive progression of "normal" eyes as a function of age. It is possible that patients are initially overcorrected and the over-correction masked by the patient's accommodative powers. With time and loss of accommodation, the hyperopia may be gradually unmasked with the hyperopia becoming visually symptomatic. At the time of surgery, a patient may be corrected with resultant slight hyperopia and yet have 20/20 vision because of the ability of the lens to accommodate. There is a range of residual correction within which the patient can have 20/20 uncorrected vision. This range varies depending on the individual but probably spans two to three diopters. Even with this range, the percentage achieving 20/20 is only 50–60%. This reflects poorly on the precision of the technique. It is important to note that this range diminishes with presbyopia, or loss of accommodation which usually begins at about 45 years of age. This results in the percentage achieving 20/20 dropping from the 50–60% described above. It is obvious that RK does not qualify as a simple, safe, predictable procedure to adjust the refractive outcome after the initial RK has been performed. Most ideas to contend with the corneal shape after this event have been purely empirical. Thus an easy method to fine-tune a refractive correction that is minimally invasive and easily at performed, would require serious consideration.

Laser stromal ablation procedures, such as photorefractive keratectomy (PRK) for correction of refractive disorders are currently popular and have had reasonable success. These procedures are not, however, spared from the problem of unpredictability. Essentially, in the treatment of myopia, laser energy is imparted to the central cornea thereby causing excision of more tissue centrally and a resultant flattening of the cornea. Unfortunately, the final refractive effect is determined not only by the amount of ablation but also by the healing response to the keratectomy. The cornea actively lays down new collagen and the epithelium undergoes a hyperplastic response, among other responses, in an attempt to repair the damage to its surface. This causes regression, or a shift backwards towards myopia, which can gradually occur over a period of months to years. An undesired effect of new collagen deposition is stromal scar formation which manifests as stromal haze and possible decrease in contrast sensitivity by the patient. This corneal stromal opacification is variously referred to as fibrosis, scarring, or haze which is associated with reduced visual acuity and contrast sensitivity, regression of the refractive effect, and poor night vision. Predictability with PRK is an issue, as with RK. Most published results of outcome after PRK treatment for myopia show 80–94% of eyes obtaining uncorrected visual acuity of 20/40 or better while the percentage of patients achieving 20/20 is significantly less. These numbers are in spite of the fact that there is a range of residual refraction at which the patient can still see 20/20 as previously explained. It can be assumed that a significant proportion of those achieving 20/20 after PRK are actually slightly hyperopic. It may very well be that with time, a significant percentage of those patients develop "progressive hyperopia," or an unmasking of the latent hyperopia. So, although the percentage of patients achieving 20/20 after PRK is not acceptable by the definition of an ideal refractive procedure, it may be inflated as was the initial results with RK. Although visual recovery is slow in RK, it is quicker than after PRK. A second laser ablation procedure is usually undertaken with caution since it may cause a greater healing response with even more regression than the initial procedure. Again, as in RK, the laser ablation procedure is not completely predictable, partly because one cannot predict an individual's wound healing response.

Excimer laser-assisted intrastromal keratomileusis (LASIK) has similar problems with predictability. High predictability is critical in any refractive surgery procedure. Predictability in refractive surgery is defined as the obtained refractive effect divided by the planned refractive effect. The planned refractive effect presently is based on nomograms that take into account a limited number of variables-usually the diameter of the ablation zone and the theoretical depth of tissue ablation. A myriad of nomograms exist that prescribe the amount of excimer laser stromal ablation for LASIK. They include the use of the standard PRK algorithms, an addition of 20% to the standard PRK algorithm, and a reduction of 20% from the standard PRK algorithm. There is no real consensus on how to predict accurately the refractive outcome, and it may be necessary for surgeons to have personalized nomograms to achieve the highest predictability.

For years it has been thought that refractive surgery with intracorneal implants could be used in the correction of ametropia. The use of synthetic intracorneal implants for the correction of refractive disorders was initially conceptualized by Barraquer in 1949. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's (keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses included surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention.

Zhivotosvskii, D. S., USSR Patent No. 3887846, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the ring are not described.

A. B. Reynolds U.S. Patent No. 4,452,235 describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia:

1. The first problem is concerned with the ability to predetermine the shape and size of a implant that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.

2. he refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area, —the inherent individual variability, in that while the outcome may be stable, it may very well be an inadequate refractive outcome that is stable.

Another unaddressed issue is that even with the implant, surgeons will aim for a slight under-correction of myopia because, in general, patients are more unhappy with an overcorrection that results in hyperopia. Again, the refractive outcome may be more stable than in RK or PRK but it may be an insufficient refractive result that is stable.

Simon in U.S. Pat. No. 5,090,955 describes a surgical technique that allows for modification of the corneal curvature by inter-lamellar injection of a synthetic gel at the corneal periphery while sparing the optical zone. He does discuss an intra-operative removal of gel to decrease the volume displaced and thus adjust the final curvature of the central corneal region.

Barrett et al. in U.S. Pat. No. 5,391,201 describes a corneal inlay ring apparatus for altering the curvature of the central optic zone of the cornea of the eye without intrusion into the optic zone. His method of implanting the ring varies from other methods described.

Siepser in U.S. Pat. No. 4,976,719 describes another ring-type device to either flatten or steepen the curvature of the cornea by using a retainer ring composed of a single surgical wire creating a ring of forces which are selectively adjustable to thereby permit selective change of the curvature of the cornea, —the adjustable means comprising a turnbuckle attached to the wire.

There are several mechanisms by which peripheral manipulation of the cornea affects anterior corneal curvature. The cornea, like most soft tissues, is nonlinear, viscoelastic, nonhomogeneous, and can exhibit large strains under physiologic conditions. The whole eye is geometrically extremely complex and the biomechanics technique capable of systematically modeling this reality is the finite element method which assumes small strains (a measure of deformity), homogeneity, and linear elastic behavior. Two simple mechanisms will be briefly described.

A simple example is helpful in understanding the first mechanism. Assume a loose rope R between two fixed points P1 and P2 as in FIG. 4($a$), which forms a curve, the lowest point P being in the middle. Referring to FIG. 4($b$), a weight W placed on the rope between the middle point P and one fixed point will cause the central portion of the rope to straighten. The cornea C demonstrated in FIG. 5($a$) and FIG. 5($b$) behaves similarly, the two fixed points, P1 and P2, analogous to the limbus of the eye and the weight W similar to the intrastromal implant 4 which, when inserted in the cornea in surrounding relation to the corneal central optical zone, causes the corneal collagen fibers to deviate upwards at (3) above the implant, and downwards at (5) below the implant. In essence, this deviation of the cornea around the peripheral implant caused by volume displacement in the peripheral cornea results in other areas of the cornea losing "slack," or relatively straightening.

The second mechanism is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called 'keratomileusis' and those involving addition received the name of 'keratophakia'. Intrastromal corneal ring add bulk to the periphery and increasing the thickness of the ring results in a more pronounced effect on flattening of the anterior corneal curvature by "increasing (thickness) in its periphery".

The goal of refractive surgeons should be to achieve 20/20 uncorrected visual acuity with long-term stability in greater than 95% of patients. None of the currently available refractive surgery procedures generate this degree of accuracy or stability.

Once again, an easy procedure to post-operatively fine-tune the refractive correction and corneal curvature which is often influenced by changes in corneal hydration status, wound healing responses, and other unknown factors, is not available. Each of the techniques described suffers from a limited degree of precision. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

SUMMARY OF THE INVENTION

The present invention concerns the use of an adjustable intrastromal device adapted for implantation in the cornea and formed of a flexible hollow shell with an annular chamber that may be augmented with a biocompatible filler material such as strands of polymethylmethacrylate (PMMA). In particular, this invention relates to the flexible hollow shell of the device. The filler material can be any biocompatible material of any shape or length but preferably is ring-shaped and a flexible elongated strand-like filament of a variable size. The annular shell of the device is filled with a predetermined amount of the biocompatible material described, and implanted in the cornea in surrounding relation to the optical zone of the cornea. The corneal curvature is then adjusted by removal of one or more strands from the implanted device thus decreasing the volume of peripheral corneal tissue displaced by the device in a discrete fashion and resulting in steepening of the corneal curvature and a myopic shift. This relatively simple adjustment for refractive correction can be performed with surgical instruments commonly available and requires minimal post-operative manipulation of the cornea and the implanted device. The apparatus of the invention is an adjustable implantable device including an outer membrane or shell forming an enclosure for receiving a filler material such as multiple rings and adapted to be inserted into the interlamellar space of the corneal stroma for the purpose of correcting refractive error. The peripheral corneal volume displaced by the device is easily modified on multiple occasions following the initial surgery of implantation and thus allows for adjustment of the refractive outcome at a later date without necessitating the removal of the implanted device. In order for the volume of the shell to be adjusted, the flexible shell must be collapsible and flatten with removal of strands. Weakening the inner and outer diameters of the shell facilitates bending of the shell at the angles and allows flattening or collapsing of the shell. In certain embodiments, the corneal ring comprises a hollow tubular shell having an arcuate shape, a shell wall and an inner arc and an outer arc. The inner arc and outer arc may have a first hinged portion extending along the inner arc, and a second hinged portion extending along the outer arc. In an alternate embodiment, the biocompatible material of the tubular shell has a material memory such that the tubular shell is biased towards a collapsed position. In another embodiment, the tubular shell comprises a first side portion and a second side portion, wherein said first and second side portions are bonded along the inner arc to form an inner seam and along the outer arc to form an outer seam, and wherein the inner seam comprises a first hinged portion and the outer seam a second hinged portion.

DETAILED DESCRIPTION OF THE INVENTION

The disclosure of the pending application Ser. No. 08/829, 846 filed Apr. 1, 1997, is incorporated herein by reference.

Figure 1:
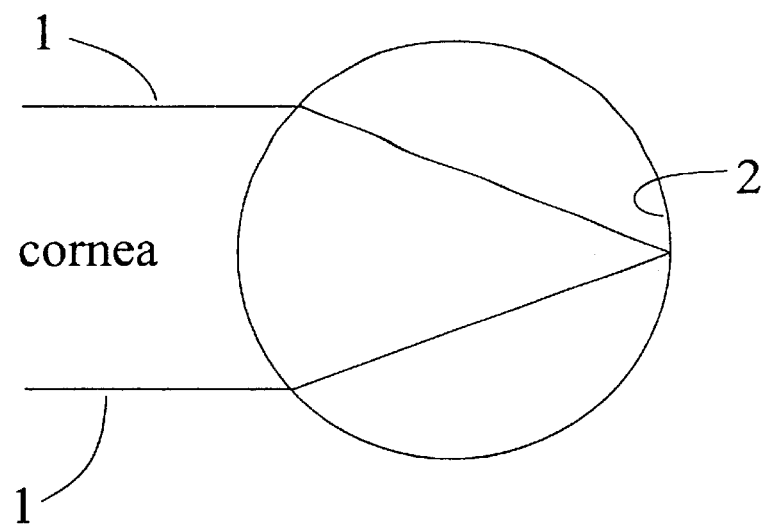
FIG. 1 is a schematic representation of a horizontal section of the human eye.
Figure 2:
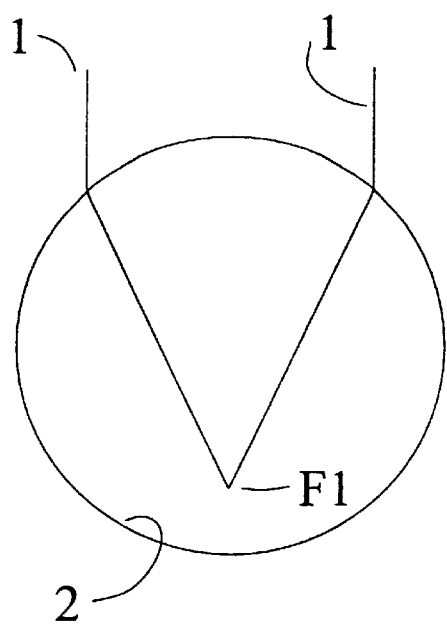
FIG. 2 is a schematic representation showing how the light rays focus in front of the retina of the eye in the condition of myopia.
Figure 3:
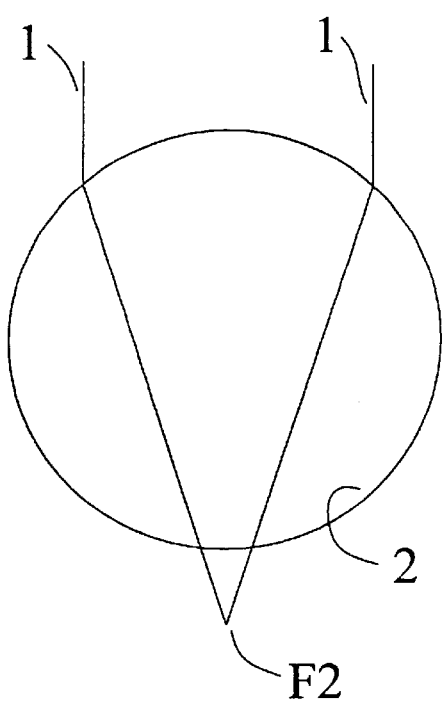
FIG. 3 is a schematic representation showing how light rays focus in front of the retina of the eye in the condition of myopia.
Figure 4A:
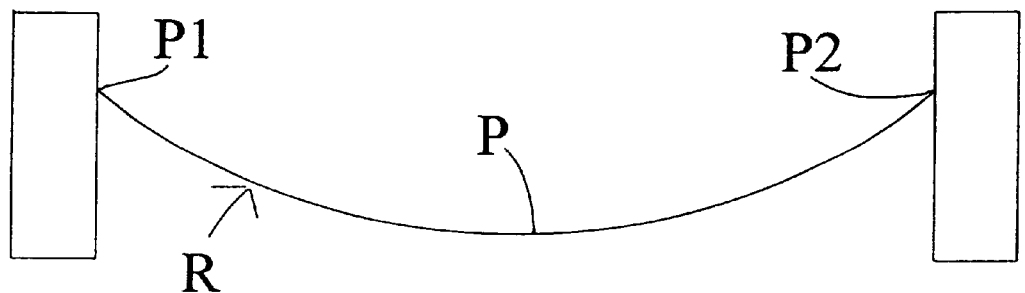
FIG. 4(a) is a schematic illustration for showing a rope suspended at its ends between two fixed points.
Figure 4B:
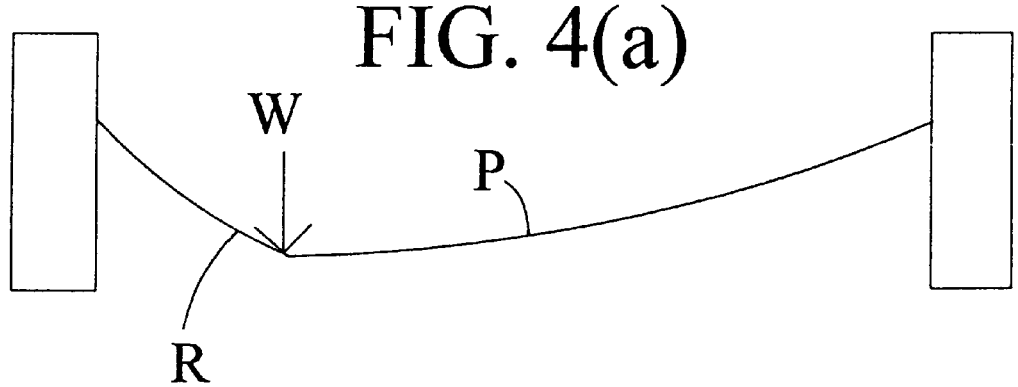
FIG. 4(b) is a schematic illustration which shows the rope in FIG. 4(a) with the force of a weight applied to the rope between its midpoint and one of the fixed points.
Figure 5A:
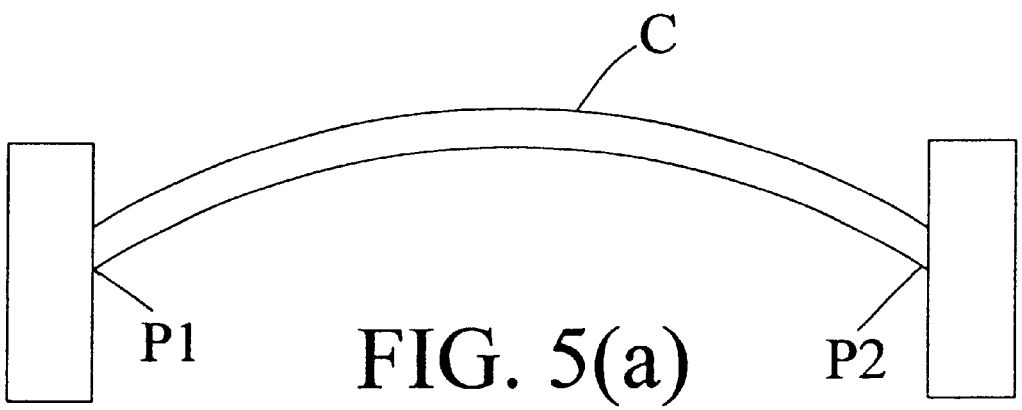
FIG. 5(a) is a schematic illustration showing the cornea of an eye wherein the cornea is fixedly attached at diametrically opposed points on the surrounding limbus.
Figure 5B:
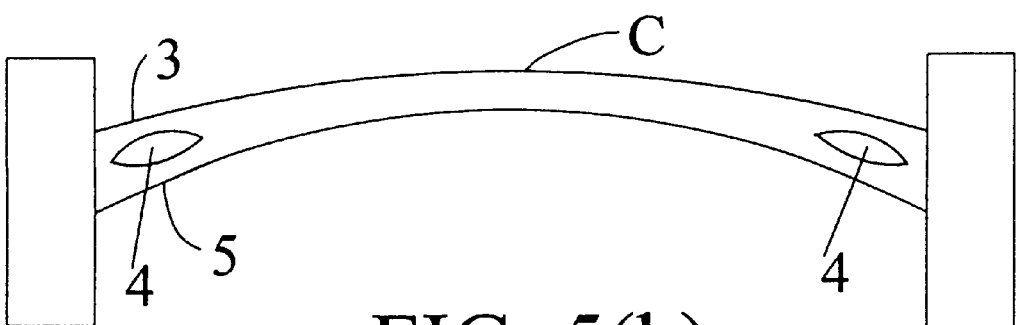
FIG. 5(b) is an illustration similar to FIG. 5 (a) but showing the curvature effects produced on the cornea because of the presence of an intrastromal support implant in the cornea.
Figure 6:
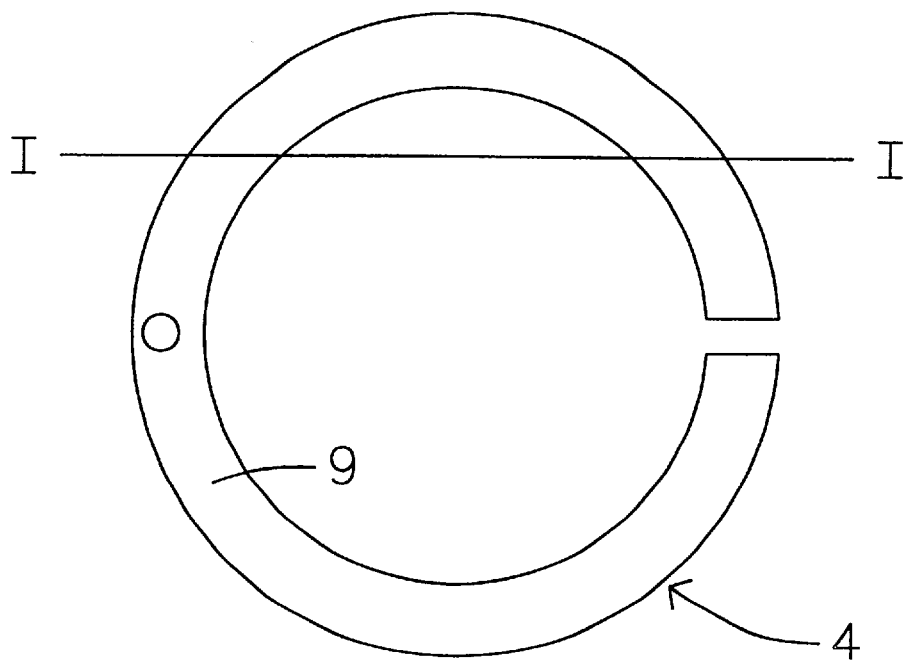
FIG. 6(a) is a plan view of the flexible device of the invention wherein the device has been severed by a radial cut.
FIG. 6(b) is a plan view of the flexible device according to another embodiment wherein the annular ring comprises two halves.
Figure 6:
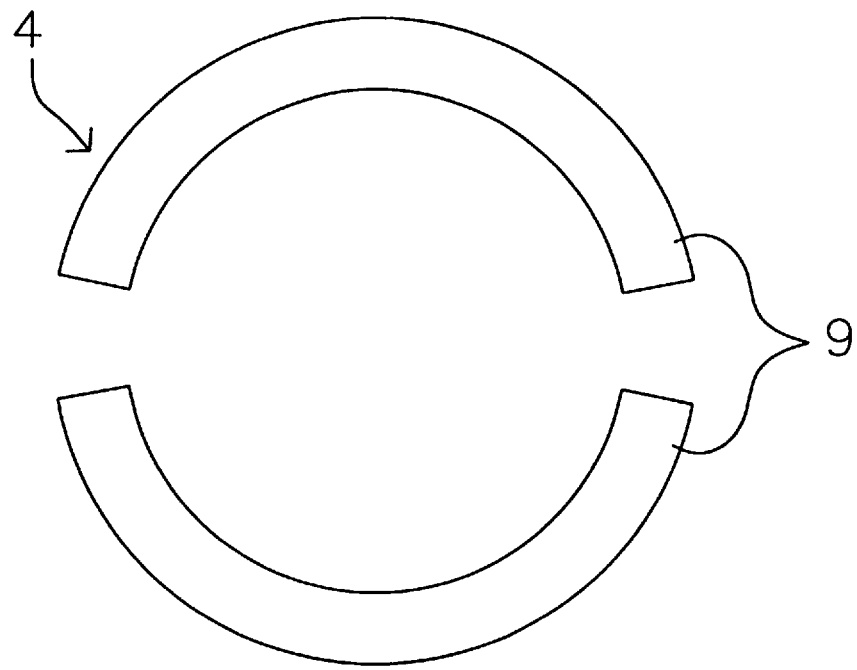

Referring more particularly to the drawings, there is shown in FIG. 6 (a) an adjustable device 4 according to one embodiment of the invention. The device 4 forms an enclosure for receiving a filler which is easily removable, such as a PMMA ring or other strand-like materials such as nylon, polypropylene, polyester, Dacron, polyamide, or other polymeric materials such as fluoropolymers. The device filler material can be any biocompatible material but preferably is a flexible, filamentous structure that may be constructed from a permanent plastic or polymeric substance such as that described above. The terms ring and strand are used interchangeably in this document. The cross section of the strand may be of various geometric shapes including circular, oval, rectangular, square, or triangle. The cross-sectional area of the strand can vary in dimension along its length. The device may contain one or more strands, each of which is removable at a later time.

Figure 9A:
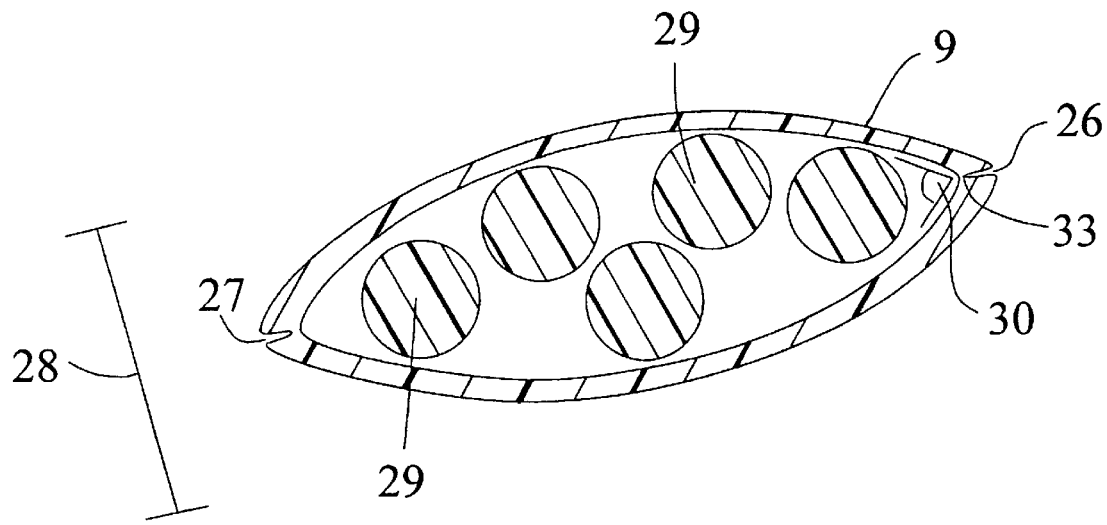
FIG. 9(a) is an enlarge radial cross section view of the perforated tubular device of the invention wherein the interior of the device has been filled with a number of rings.
Figure 9B:
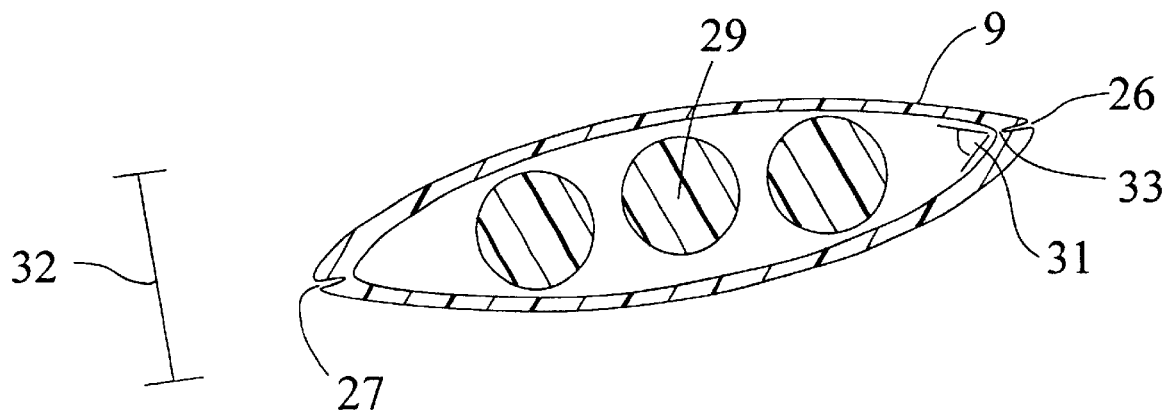
FIG. 9(b) is a cross section similar to FIG. 9(a) but wherein some of the rings shown in FIG. 9(a) have been removed from the device.

The device 4 comprises a tubular shell 9 made of a flexible material, such as a silicone, acrylic or urethane polymer and in FIG. 6(a) is shown as a split donut shape. The ideal arc length of the shell is 345°+/−15°. However, in sub-embodiments, the shell and corresponding inner strands may have an arc length of approximately 160°+/−15° (FIG. 6(b) such that two halves of an annular device are implanted in the lamellar channel opposite to each other. The shell material has adequate stiffness such that the device will maintain its generally circular shape in plan view when sufficiently filled and also have adequate flexibility to allow an increase in a radial cross-sectional area with filling as shown in the cross section view of FIG. 9(a) and a decrease in radial cross-sectional area with removal of the strand as shown in FIG. 9(b). The shell of the device has sufficient structural integrity, strength and flexibility to generally maintain its circular shape and be expandable.

The composition material of the annular shell may any suitable plastic or polymer material such as that used in producing foldable or deformable intraocular lenses, silicone polymers, urethane polymers, acrylic polymers, polyesters, fluoropolymer resins, or materials used in soft contact lenses. It will be understood by those skilled in the art that, among polymers of acrylic esters, those made from acrylate ester monomers tend to have lower glass transition temperatures and to be more flexible than polymers of methacrylate esters. Examples of other medical devices composed of materials which may be suitable for the shell of this invention include vascular graft tubing, dialysis tubing or membrane, blood oxygenator tubing or membrane, ultrafiltration membrane, intra aortic balloon, catheter, suture, soft or hard tissue prosthesis, artificial organ, and lenses for the eye such as contact and intraocular lenses.

The essence of the invention is an annular device that is implanted intrastromally in the peripheral cornea thus inducing flattening of the central corneal curvature and that is designed such that the amount of peripheral corneal tissue it displaces can be easily modified at a later time in a minimally invasive fashion to thus adjust the refractive effect. Two essential factors which are crucial to the feasibility of the device are 1) biocompatibility without significant biodegradation of the device and 2) collapsibility of the outer annular shell following strand removal. These two factors are discussed in detail in the following discussion.

The composition material of the device, both outer annular shell and inner strands, is a biomaterial. A "biomaterial" may be defined as a material that is substantially insoluble in body fluids and that is designed and constructed to be placed in or onto the body or to contact fluid of the body. Ideally, this biomaterial will have the following characteristics:

1. It will minimally induce undesirable reactions in the cornea such as an inflammatory reaction.

2. It will have the physical properties, such as strength, elasticity, and flexibility required to function as intended.

3. It can be purified, fabricated, and sterilized easily.

4. It will substantially maintain its physical properties and function as intended during the time that it remains implanted in the cornea, whether it be an hour or a lifetime.

As used herein, the surface of a biomaterial is characterized as "biocompatible" if it is capable of functioning or existing in contact with tissue of a living organism with a net beneficial effect on the living organism. Long-term biocompatibility is desired for the purpose of reducing disturbance of the host organism.

A number of approaches have been suggested to improve the biocompatibility of implants. One approach has been to modify the surface of a biomaterial. A biocompatible surface can be formed of a plurality of separate molecules of a biocompatible agent covalently linked, through a linking moiety, to the surface of a biomaterial to provide that surface with substantially the same biocompatible characteristics as are possessed by the biocompatible agent. Guire in U.S. Pat. No. 4,973,493 extensively references and describes surface modification techniques to modify solid surfaces to improve its biocompatibility characteristics. There are various techniques available to improve biocompatibility of materials by surface modification and other techniques. Current technology includes HydroLAST™, ParyLAST™, Hydak™, and Photolink technology which in various degrees enhance surface characteristics to achieve wettability, lubricity, hemocompatibility, microbial resistance, and surface passivation.

Surface modifications are being widely explored to enhance the biocompatibility of biomedical devices and improve other aspects of performance. If the material of the device of the invention has appropriate performance characteristics and physical properties but moderate to poor biocompatibility, surface modification provides a means to alter the biocompatibility of the device without the need for redesigning the device using alternative materials. Materials can be surface modified by using biological or physicochemical methods. Modification can also be achieved by creating surface texture or roughness. The advantages of surface modification for biomaterials include influence on cell adhesion and growth, control of protein absorption, improvement of lubricity, and improved corrosion resistance.

Surface modification methods used on polymers include noncovalent coatings, covalently attached coatings, gas phase deposition, chemical grafting, biomolecule immobilization, etching of the original surface, and chemical reactions such as nonspecific oxidation, functional group modifications, and addition reactions. These methods are reviewed in detail in the text by Buddy Ratner, Biomaterials Science pgs. 105–118.

Surface modification of the biomaterial to be used in the device of the invention also aids in preventing infection. Infection around biomaterials and damaged tissues is caused by bacterial adhesion to those surfaces. Surfaces well colonized by healthy tissue cells tend to be resistant to infection. The colonization potential of most synthetic surfaces for bacteria is high compared with tissue cells because such surfaces are acellular, inanimate, and resemble substrata in nature. It is logical that infection may be prevented by encouraging colonization (integration) of material surfaces by healthy tissue cells, which then occupy available binding sites on biomaterials and form a new layer somewhat resistant to bacterial colonization. Most important for each material is the surface interaction of the outer atomic layers with environmental moieties, glycoproteins, elemental constituents, or various cells. Ideally, we would like to influence interactions to promote compatibility and/or integration and resistance to infection. Conditioning protein molecules play a variety of roles in bacterial adhesion, depending on their concentration and environmental condition. For example, bacterial adhesion is decreased by the presence of albumin. The surface of the device of the invention can be modified by advanced techniques that create a known interface response based on programmed surface quantum states, directing desired molecular or cellular interactions. Heavy ion implantation, chemical vapor deposition, and vacuum evaporation may be used to create a surface that "directs" tissue or macromolecular integration to build a tissue system, rather than bacterial adhesion. All the previously described technology may be applied to the device of the present invention to increase its biocompatibility.

The collapsibility of the outer annular shell following removal of strands from the implanted device is important in effecting the refractive adjustment. FIG. 9(a) and 9(b) demonstrates what is meant by collapsibility of the shell; a decrease in radial cross-sectional area and thickness (28 to 32) following removal of strands from the shell of the device. Factors that determine ease of collapsibility of the shell following removal of strands from the shell include shell wall thickness, wall material composition, flexibility of the material, the memory of the material, and these characteristics of the material at the angle of the inner and outer diameters of the shell. The wall material 33 at the inner and outer diameter angles provide the bulk of the structural integrity which resists shell collapse or flattening. Collapsibility of the shell can be promoted by decreasing wall thickness, thus decreasing the structural mass at the inner and outer diameters which maintain the angle. Collapsibility can be facilitated by forming the shell of a material softer in composition or with less flexural strength.

Figure 7A:
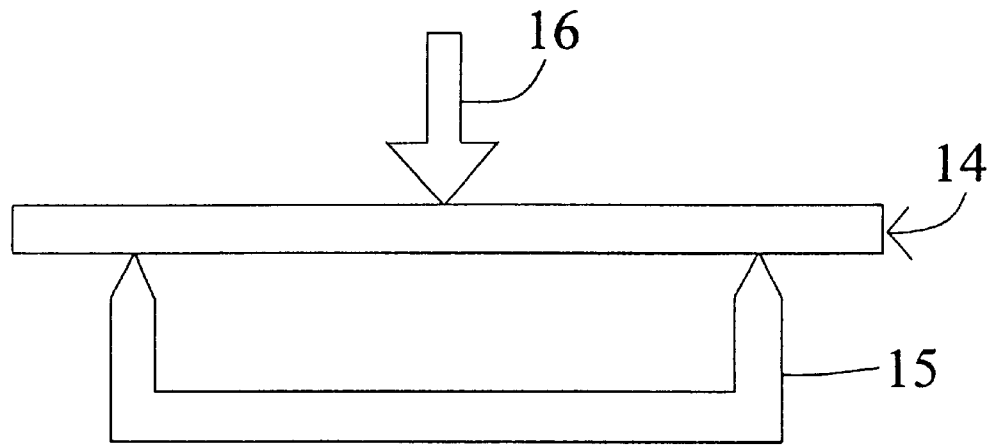
FIG. 7(a) is a schematic illustration showing a method used to test flexural strength of a plastic specimen on a test support.
Figure 7B:
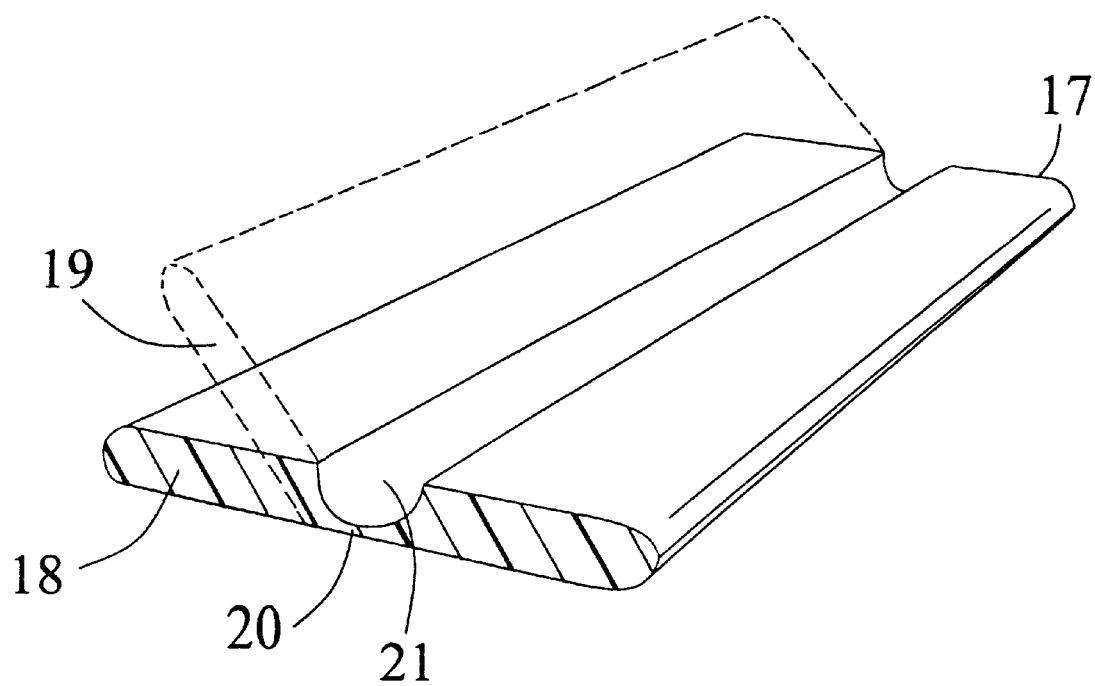
FIG. 7(b) is a schematic representation of a flexible (integral) hinge demonstrating its flexible nature.

One method to facilitate collapsibility is to decrease the flexural strength at the inner and outer diameter angles. Referring to FIG. 7(a), flexural strength is a measure of how much stress or load 16 can be applied to a material before it breaks. Both tensile and compressive stresses are involved in bending the sample. Because most plastics do not break when deflected, the flexural strength at fracture cannot be calculated easily. The ISO (International Organization for Standardization) procedure varies the span of supporting blocks 15 on which the sample 14 is placed according to the thickness of the sample. The load 16 is applied in the center. In this method of measurement, the force is measured when the deflection equals 1.5 times the thickness of the sample. A common example of a method to decrease the flexural strength is shown in FIG. 7(b). The integral or flexible hinge 17 has a groove 21 that is positioned along the center of the anterior surface. This area of decreased thickness 20 decreases its flexural strength and allows it to bend more readily, permitting the "hinge" action (position 18 to position 19).

Figure 8:
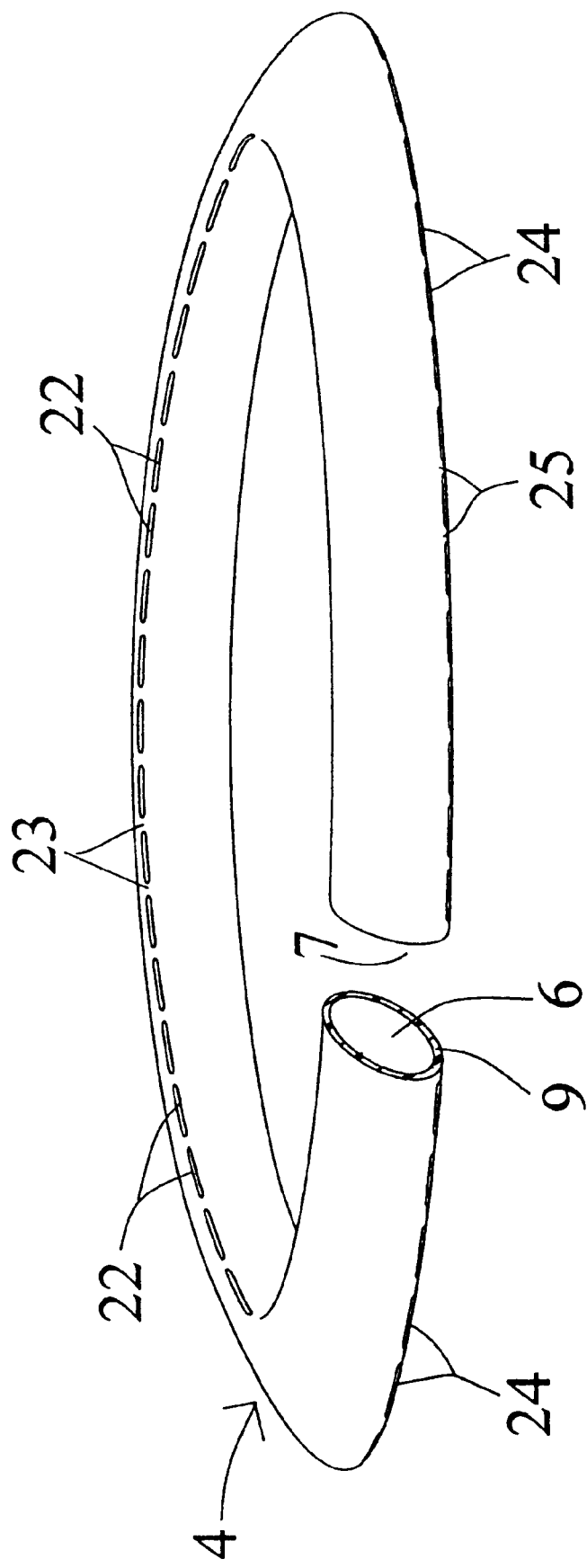
FIG. 8 is a perspective view of the outer shell of the invention demonstrating perforation along the inner and outer diameters of the shell.

Referring to FIG. 8, collapsibility of the shell 9 can also be facilitated in a similar manner by perforating the inner and outer diameters of the shell thus decreasing the resistance to flattening and effectively decreasing the amount of shell wall material at the inner and outer diameters which provide the resistance to flattening. The flexural strength of the shell at the inner and outer diameters is effectively decreased. Both the inner diameter perforations 22 and outer diameter perforations 24 are directed horizontally and separated by intact areas (23 and 25). The illustrated perforations are completely through the wall of the shell. Perforation of the areas described allows the wall thickness to be increased without sacrificing collapsibility of the shell and also allows slightly stiffer materials to be used in making the shell without compromising shell collapsibility with strand removal.

The perforations may completely penetrate the wall thickness or, according to an alternate embodiment, may only be partial wall depth 26, 27 as shown in FIGS. 9(a) and (b). In this embodiment, the perforation at 26 makes a hinge portion in the corneal ring along the inner arc of the corneal ring, and the perforation at 27 makes a hinge portion in the corneal ring along the outer arc of the corneal ring. The perforations when only partial wall depth may be joined such that the perforation is continuous. When perforations are only partial wall depth, it is referred to as a groove. The groove may be made at any depth ranging from 10% depth to 90% depth, depending upon the material used and may be continuous around the inner and outer diameters of the annular shell. A combination of a groove and complete perforations may be used in situations where grooving is difficult for technical reasons or inadequate in facilitating collapsibility.

The perforations along the inner and outer diameters of the shell can be produced using a sharp instrument or with a laser, however, lasers are preferable. Lasers are used to make intricate holes and complex patterns in plastics. The laser power can be controlled to merely etch the plastics surface or actually vaporize and melt it. Holes and cuts made by a laser have a slight taper, but the cuts are clean with a finished appearance. Cuts made by a laser are more precise, and tolerances are held more closely than those made with conventional machining operations. There is no physical contact between the plastics and the laser equipment, therefore no chips are produced. Laser cutting does produce a residue of fine dust; however, this is easily removed by vacuum systems. Most polymers and composites may be laser machined.

Thus, a material with less flexibility may be used to produce the annular shell and undergo perforation of the inner 26 and outer 27 diameters. The concept of weakening the structural support at the inner and outer diameters allows less flexible materials to be used in the production of a collapsible annular shell. Certain materials that are more ideal may be flexible and collapsible at a given wall thickness but because of manufacturing limitations, production at the required wall thickness may be impossible. In this situation, the annular shell is produced at the increased thickness and the inner and outer diameters of the shell perforated or weakened as described. Thus, materials that are limited by manufacturing capabilities but having other favorable characteristics such as permanence, stability, lack of discoloration, and biocompatibility can be formed into an annular shell device having the important collapsibility feature.

Another method to facilitate outer shell collapse involves the plastics concept of fatigue. Fatigue is a term used to express the number of cycles a sample can withstand before it fractures. Fatigue fractures are dependent on temperature, stress, and frequency, amplitude, and mode of stressing. If the load (stress) does not exceed the yield point, some plastics may be stressed for a great many cycles without failure. In the manufacture of integral or flexible hinges, the fatigue characteristics of the plastics are often considered. These flexible hinges are tested with a folding endurance tester, which records on a dial the number of flexings that take place before a plastics sample breaks. This concept is useful in producing a collapsible shell.

In the example of a flexible hinge, the greatest resistance to bending occurs in the first few cycles (varying depending upon the material used). As the hinge "fatigues", the resistance to bending progressively decreases. In like fashion, with the outer shell, the inner and outer diameters are analogous to the hinge with collapse of the shell closing the hinge and expanding the shell opening the hinge. If the outer shell undergoes multiple cycles of collapse and expansion, the resistance at the inner and outer diameters decreases. Because at most only a few cycles of shell collapse and expansion are likely to be required once the device is implanted in the cornea, partially "fatiguing" the shell is another method to decrease the flexural strength at the inner and outer diameter angles prior to implantation and thus facilitate shell collapse.

In another method to facilitate shell collapse, the outer shell may be collapsed or flattened and then the inner and outer diameters heated such that the shell's native position is to be collapsed. After the strands are placed inside the shell and the device implanted into the cornea, when the strands are removed from the shell, because of material memory, the shell returns to a collapsed position.

Figure 10A:
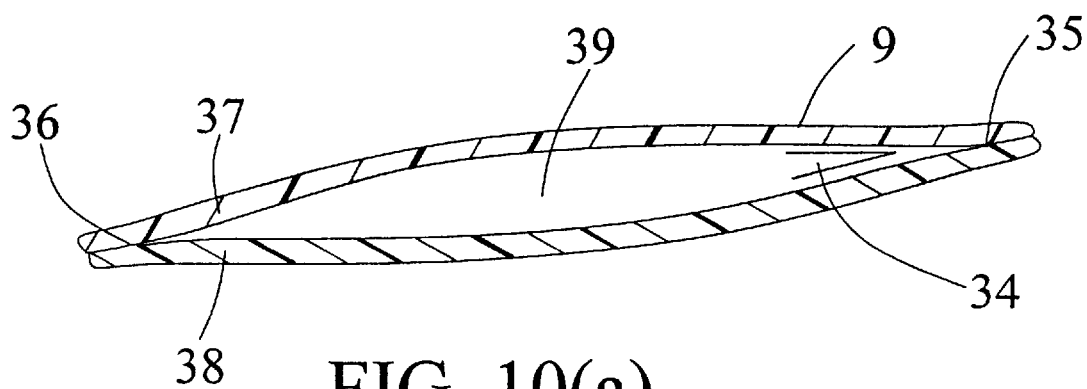
FIG. 10(a) is a radial cross section view of the outer shell of the invention.

In yet another method to facilitate annular shell collapse following strand removal from an implanted device, material memory is relied upon. Referring to FIG. 10(a), which illustrates a radial cross-section of an empty annular shell, the shell is composed of an upper annular membrane or wall 37 and a lower membrane or wall 38. The two halves are joined at the inner 35 and outer 36 diameter edges by any number of means. The two halves are attached at the edges by various means including chemical adhesion, and frictional heating techniques such as high-frequency bonding and ultrasonic bonding. Dielectric or high-frequency bonding is used to join plastics films, fabrics, and foams. Only plastics that have a high dielectric characteristic (dissipation factor) may be joined by this method. ABS, polyvinyl chloride, polyether, polyester, polyamide, and polyurethane have sufficiently high dissipation factors to allow dielectric sealing. Fluoroplastics have very low dissipation factors and cannot be heat sealed electronically. The actual fusion is caused by high-frequency waves from transmitters or generators. In the areas of the parts where the high frequency waves are directed, molecules try to realign themselves with the oscillations. This rapid molecular movement causes frictional heat and the areas become molten. Referring again to FIG. 10(a), if dielectric bonding is used to join the upper and lower half edges, a thin annular ring of a fluoroplastic material may be placed between 39 the halves preventing the halves from being joined in that area. In this embodiment, the upper annular membrane 37 and the lower membrane 38 form an inner seam and an inner seam where they are joined. The inner seam comprises a first hinged portion and the outer seam comprises a second hinged portion.

Figure 10B:
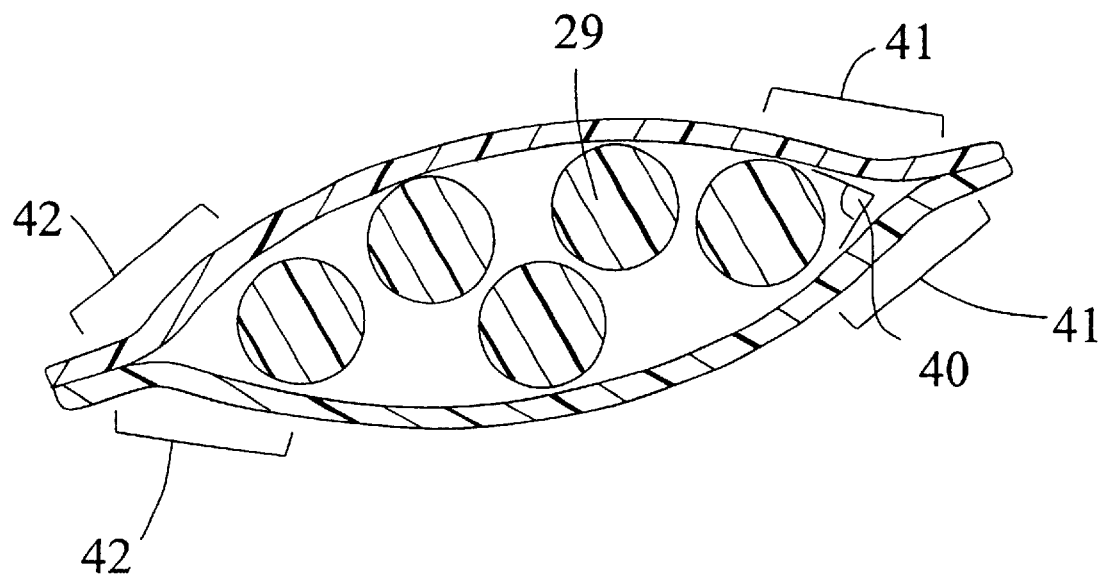
FIG. 10(b) is a radial cross sectional view of the shell of FIG. 10(a) filled with strands.
Figure 10C:
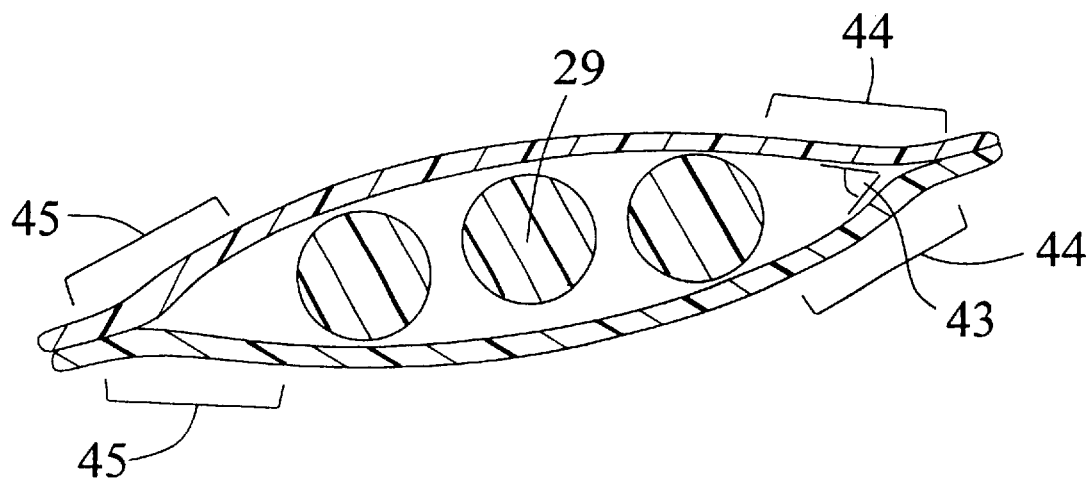
FIG. 10(c) is a radial cross sectional view of the shell of FIG. 10(b) with some strands removed.
Figure 11A:
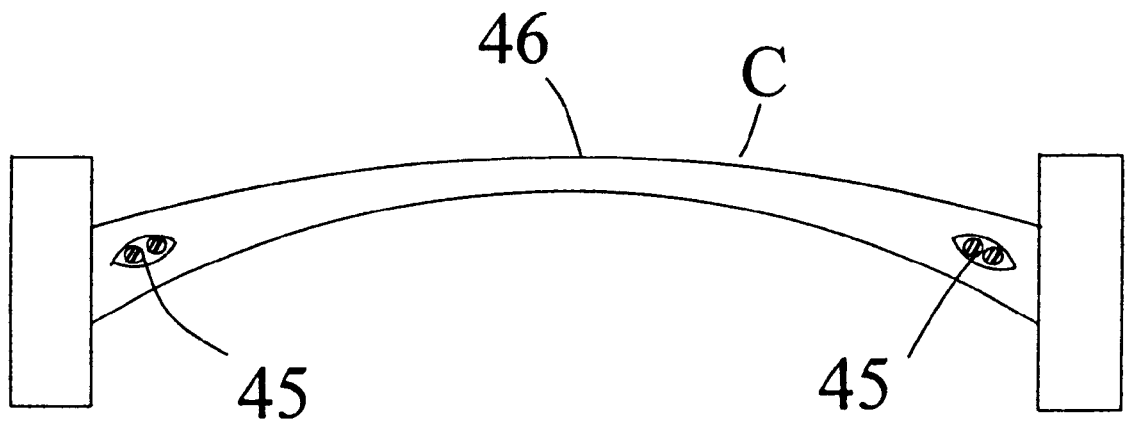
FIG. 11(a) and 11(b) show cross-sectional view of the therefrom.
Figure 11B:
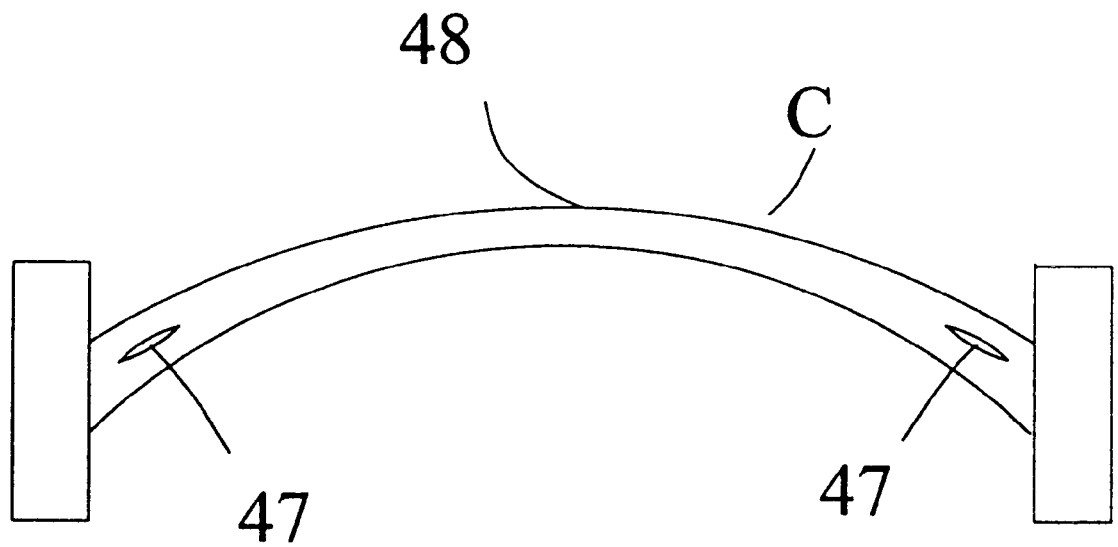

Referring to FIG. 10(b), the annular shell from FIG. 10(a) is filled with strands 29 which causes the annular shell areas around the inner 41 and outer 42 diameters to relatively flex. The angle 40 is increased compared to the shell's normal state angle 34. When the strands are removed from the shell as shown in FIG. 10(c), the flexed areas attempt to return to their original position and relatively straighten because of material memory, as shown in 44 and 45 resulting in a smaller angle 43 and a radial cross-sectional area that is smaller in FIG. 10(c) compared to FIG. 10(b).

This method does not attempt to weaken the inner and outer diameter shell but rather redirects the inherent material forces such that the annular shell favors a collapsed position unlike annular shells that have an oval radial cross-sectional shape which favor an expanded position. Again, materials that are limited by manufacturing capabilities but having other favorable characteristics such as permanence, stability, lack of discoloration, and biocompatibility can be formed into an annular shell device having the important collapsibility feature following strand removal from an implanted device.

Figure 12:
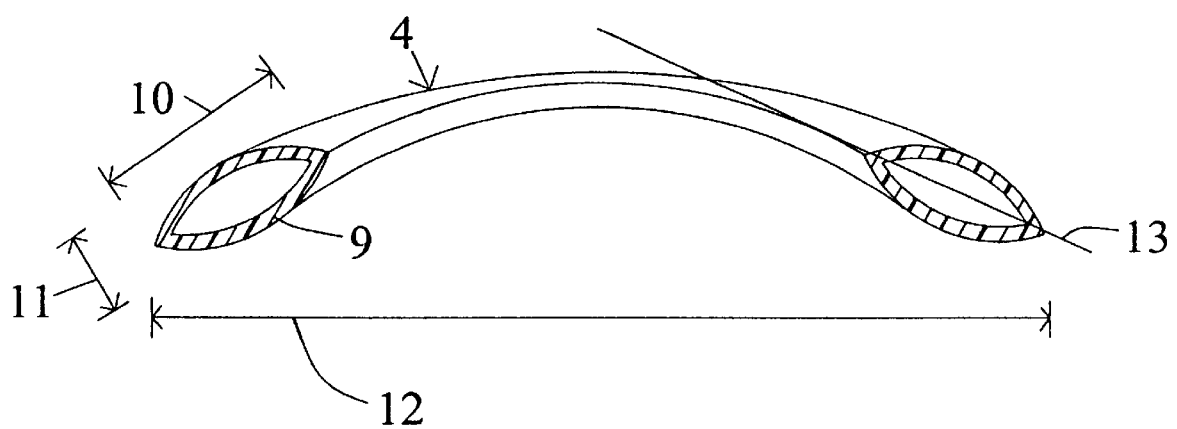
FIG. 12 is an enlarged diametral cross section view as taken along the section line I—I in FIG. 6(a).

The device 4 is adapted to be implanted into the peripheral stromal cornea. It is of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea intrastromally and consists of a flexible material which is biocompatible, and more specifically, compatible with ocular tissues. The dimensions as shown in FIG. 12 include a thickness 11 of 0.1–1.5 mm, width 10 of 0.4 to 2.0 mm and an outer over-all diameter 12 of 6.00 to 11.0 mm. The thickness of the shell 9 of this device 4 may be varied. The device may contain only one or multiple rings of varying diameter, geometrical cross-sectional shape, and composition. The ring may be composed of a permanent biocompatible material such as polymethylmethacrylate, nylon, polyester, or polypropylene and can vary from 0.02 mm in diameter to 1.0 mm in diameter. The ring may be clear or colored. The ring may be marked towards the head and tail end of the device to aid the surgeon in adjusting the tension when connecting the ends of a ring.

The size of the device chosen should be such that the range of over-correction or under-correction secondary to individual variability of response to surgery may be comfortably corrected (not requiring removal of all of the strands) by the methods described. The maximal radial cross-sectional area, and circumference, is chosen prior to insertion of the implant. The ideal embodiment, given the preoperative refractive state and other pertinent data, is chosen prior to operating and then that embodiment further manipulated as necessary to determine the ideal curvature. The device is inserted into the peripheral cornea at an adequate depth and then further adjusted in order to more precisely adjust the shape of the cornea and focus the light entering the eye on the retina. The intra-operative keratoscope or automatic keratometer may be helpful. However, intra-operative curvature measurements in surgeries involving the cornea have not been shown to be predictably reproducible.

The device is implanted into a circular lamellar channel formed at ½ to ⅔ corneal depth with a circular dissecting instrument that requires only a small midperipheral corneal incision. A knife is used to make an approximately 2 mm radial incision beginning at 2.5 to 3.5 mm from the corneal center. The surface of the cornea is cut only at this incision. A Suarez spreader is introduced into the bottom of the incision and a small lamellar channel created. Application of a vacuum centering guide is used to fix the globe while an 8–9 mm outer diameter lamellar channeling tool introduced through the incision into the lamellar channel is rotated to produce a 360° channel around the corneal mid-periphery at ½ to ⅔ corneal depth. After the channeling tool is removed, a circular endoscopic-type forceps or a circular instrument with a hook at the end is inserted into the same channel and rotated 360° such that the forcep tip or hook emerges from the radial incision. One end of the device is inserted into the forceps, the forcep jaws closed thus gripping the device, the circular forceps rotated until the device is progressively pulled into place. Alternatively, if the circular hooked instrument is used, the hook is attached to a loop pre-formed on the head of the device and the circular hooked instrument rotated until the device is progressively pulled into place. The head and tail of the device are brought together and may be fixed together with suture or glue.

Preoperatively, variables such as device circumference, radial cross-sectional area, height, width, wall thickness, biomaterial, number of strands, composition of strands, diameter and shape of strands, are chosen using nomograms developed from retrospective studies as a guide to the selection of each variable.

Post-operative adjustment are simply and easily performed and avoid the complications of re-operation concomitant with most kerato-refractive procedures. This post-operative adjustment can compensate for an inadequate preoperative implant choice, for corneal hydration intra-operatively which results in a different corneal curvature after corneal hydration status changes post-operatively, for an unexpected wound healing response in the periphery to the implant, and for later refractive changes caused by unknown factors. This postoperative adjustment is made possible by a flexible corneal device containing several rings or strands which can easily be removed thus modifying the volume of the device and resulting in increased central corneal curvature. Ring removal from the device minimally disturbs the device-stromal interface compared to removing the device itself, thus minimizing the effects wound healing and edema will have on the adjustment. This postoperative adjustment appears to be a necessary adjunct to any method that seeks to meet the criteria for the ideal kerato-refractive procedure.

A typical adjustable device 4 according to a preferred embodiment of the invention has the following dimensions. The width of its outer diameter is 0.85 mm, overall thickness is 0.3 mm, larger inner diameter is 0.75 mm, and minor diameter is 0.20 mm. A device of this size is expected to correct myopia by approximately 3 diopters. Devices of lesser radial cross-sectional area are calculated to correct a smaller amount of myopia and devices of greater radial cross-sectional areas are calculated to correct a greater diopteric amount of myopia. Of course, a particular individual may not have the exact same outcome for a given device size as another individual. To calculate the number of rings which will comfortably fit and the diopter change with removal of each ring, the following is assumed for a device of 0.3 mm thickness. The cross-sectional area of the oval-shaped device is approximately 0.11 mm squared. Since this volume cannot be completely filled with rings that have round cross-sections because there are spaces between the round rings, the area that will be occupied by a ring is 78.5% ideally. Approximately four 0.175 mm diameter rings or seven 0.125 mm diameter rings will fit into this space. Complete removal of all rings results in flattening by 0.2 mm or a 2.0 Diopter change. The average diopter change for each 0.175 mm diameter ring removed from this typical embodiment is 0.5 diopter, for each 0.125 mm diameter ring removed, 0.3 diopter change. Given an initial myopic patient, the outcome can be overshot by 50% of the initial refraction and the hyperopia still reasonably managed by ring removal alone. Over-treatment resulting in hyperopia is a significant disadvantage in most kerato-refractive procedures. In radial keratotomy the wound healing processes occur over a period of years and there is often a progressive hyperopia. Patients who become symptomatically hyperopic after surgery are extremely unhappy. Therefore most surgeons use nomograms that attempt to achieve a slight under-correction. Concerning photorefractive keratectomy, in one study, it was found the main reason patients did not have their second eye corrected with PRK (given that their first eye was corrected with PRK) was because of dissatisfaction with the hyperopia in their operated eye. The technique described herein easily corrects over-correction hyperopia.

This particular sub-embodiment may be used with any of the previous processes described. An important advantage of this design is the ease of reversibility of the procedure. The procedure may be completely reversed by the surgical removal of the device or the refractive effect may be partially altered as previously described. The adjustments themselves may be reversed.

It is therefore to be appreciated that by use of the various embodiments of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well-suited to adjust a hyperopic refractive outcome. 2) Irreversibility of radial keratotomy and laser ablation surgeries. 3) Surgical manipulation of the central visual axis with the potential for scar and stromal haze formation following laser ablation procedures. 4) The need for chronic use of steroid drops with its accompanying complications such as cataract and glaucoma. 5) Regression with laser ablation procedures, especially following re-operation. 6) Reduction of positive sphericity with RK and laser ablation which may result in increased image aberration. 7) The invasiveness of laser in-situ keratomileusis. 8) Lack of precision and predictability with all current procedures. 9) The possible need for repetitive explanting and implanting of ICR'S, which may cause shearing of corneal peripheral channel lamellae with associated decrease in effect and also scar formation.

The last point requires further elaboration. Methods to adjust ring thickness have been described in the prior art. These methods are only discussed in relation to adjusting the ring thickness during implantation, not post-operatively. Attempts to adjust the thickness of the ring are most useful after corneal curvature has essentially stabilized. Adjustments of devices that have been described in the prior art would necessarily require rotation of the ring with resultant shearing of the corneal-ring interface. Rotation of the ring would be required to allow more or less overlap of the individual ring parts thus increasing or decreasing ring thickness. This shearing of the corneal tissue in the immediate vicinity of the ring may alter the corneal curvature in an unpredictable fashion and probably also induce more scarring with possible unpredictable long-term effects. In the embodiments described above, the device volume is adjusted with only very minimal disturbance of the surrounding tissue. By the nature of the adjustment, there is no rotational movement of the aspect of the device which is in contact with the corneal tissue with respect to the cornea. The corneal-device interface is essentially undisturbed. Of course, with a decrease in the volume of the device, there will be a minute shift of surrounding tissue. In conclusion, a slight decrease in device volume by the adjustment described will not only be much easier to perform, but also have a much more predictable effect.

Dr. R. Eiferman in the Journal of Refractive and Corneal Surgery states-that "if we can regulate the amount of tissue that is either added to or subtracted from the cornea and control the biological response, we may then be able to optimize refractive surgery". The ideal method to control the biological response is to minimally disturb corneal tissue, thus minimally inciting a wound healing response.

Dr. K. Thompson, in the same Journal asks "will it be possible for a refractive surgery technique to bypass the variable effects of corneal wound healing altogether?" That is unlikely for any initial keratorefractive procedure but the adjustable corneal ring of the present invention makes possible an adjustment that avoids the variable effects of corneal wound healing by minimally disturbing corneal tissue.

Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. The device according to the embodiments of the present invention allows for the fact that individual tissue response to the calculated correction may not be completely predictable, and permits easy adjustments at the time of surgery and more importantly, at a later date after corneal hydration and wound healing responses have stabilized by simple ring removal from the device or replacement. The nature of these adjustments minimally disturb the implant-corneal interface (unlike the explantation of the ICR) and is thus expected to have a much more predictable effect than even the implantation of the device itself which causes less of a wound healing response than current procedures such as RK and PRK. In addition, when correcting myopia, a hyperopic outcome is very difficult to correct with any of the current kerato-refractive procedures and over-correction of myopia does occur. In this invention, a hyperopic outcome is relatively easily reversed by ring removal from the implanted device. Typically, in most kerato-refractive procedures for myopia, the surgeon aims for a slight under-correction because of the wish to avoid a hyperopic outcome. The ease with which a hyperopic outcome is adjusted with the device of the present invention enables the surgeon to aim for full correction, thereby obtaining the full benefit of the nomogram, and resulting in a higher percentage of patients with the desired refractive outcome even without a modification of the device. The surgeon may even choose to slightly overcorrect followed by a modification.

The essence of this invention lies in the assumption that individual responses to any kerato-refractive surgical procedures are variable, that even a "perfect" nomogram will not lead to a reliably predictable result in a particular individual, that a simple, safe, and effective technique for corneal curvature adjustment is necessary and that this modification should minimally disturb surrounding tissue thus allowing for a predictable effect. It should also be easily accomplished at some post-operative date after implantation of the device and after factors affecting corneal curvature changes have stabilized. A key feature of this invention lies in the ability of the device in its various embodiments to have its volume modified with ease at the time of implantation but more importantly on multiple occasions thereafter by simple removal of ring material from the implanted device, thus allowing fine-tuning of the refractive outcome.

In conclusion, in correcting refractive errors with this technique, the feeling of finality does not set in even with an initial inaccurate correction, with inadequate adjustment, or even when the last ring is removed because the device itself can be easily removed or better yet, left in place while other refractive procedures, such as laser ablation surgery are considered, if that point is ever reached.

It is also to be appreciated that the foregoing description of the invention has been presented for purposes of illustrations and explanation and is not intended to limit the invention to the precise form of apparatus and manner of practice described herein. It is to be appreciated therefore, that changes may be made by those skilled in the art without departing from the spirit of the invention and the scope of the appended claims.

What is claimed is:

1. A corneal implant comprising:
   an elongated, hollow tubular shell having an arcuate shape along the elongated portion of the tubular shell, and a shell wall comprising:
   an inner arc and an outer arc;
   a first hinged portion extending along the inner arc; and
   a second hinged portion extending along the outer arc.

2. The corneal of claim 1 wherein the tubular shell has an arc length of between about 330° and 360° along the elongated portion of the tubular shell.

3. A corneal implant comprising:
   a plurality of hollow tubular shells having an arcuate shape along the elongated portion of the tubular shells, and a shell wall, wherein each tubular shell comprises:
   an inner arc and an outer arc,
   a first hinged portion extending along the inner arc; and
   a second hinged portion extending along the outer arc,
   wherein each tubular shell has an arc length of between about 145° and 175°.

4. The corneal inplant of claim 1 further comprising a strand in the hollow of the tubular cavity, the strand extending at least partially along the arcuate length of the tubular shell.

5. The corneal implant of claim 1 wherein the first and second hinged portions each comprise at least one perforation in the wall, wherein the perforation has a deepest portion, and wherein at the deepest portion of the perforation the wall has a thickness between about 10% and 90% of a wall thickness of a portion of the tubular shell adjacent the first and second hinged portions.

6. The corneal implant of claim 5 wherein the perforation on the inner arc extends substantially along the inner arc, and the perforation on the outer arc extends substantially along the outer arc.

7. The corneal implant of claim 1 wherein the first hinged portion comprises a plurality of perforations in the wall of the tubular shell along the inner arc and wherein the second hinged portion comprises a plurality of perforations in the wall of the tubular shell along the outer arc.

8. The corneal implant of claim 7 wherein the perforations have a deepest portion, and wherein at the deepest portion of the perforations the wall has a thickness between about 10% and 90% of a wall thickness of a portion of the tubular shell adjacent the first and second hinged portions.

9. The corneal implant of claim 8 wherein the perforation on the inner arc extends substantially along the inner arc, and the perforation on the outer arc extends substantially along the outer arc.

10. The corneal implant of claim 1 wherein the tubular shell comprises a first side portion and a second side portion, wherein said first and second side portions are bonded along the inner arc to form an inner seam and along the outer arc to form an outer seam, and wherein the inner seam comprises the first hinged portion and the outer seam the second hinged portion.

11. A method for making a collapsible corneal ring from an arcuate tubular shell having a substantially uniform wall thickness along its arcuate length, the method comprising the steps of:
   removing material from the wall of the tubular shell along an inner arc of the tubular shell to form a first hinged portion;
   removing material from the wall of the tubular shell along an outer arc of the tubular shell to form a second hinged portion; and
   pre-fatiguing the tubular shell at the first hinged portion and the second hinged portion by cycling the tubular shell through at least one fatigue cycle, said fatigue cycle comprising the steps of:
   compressing the tubular shell into a collapsed position; and
   releasing the tubular shell.

12. The method of claim 11 further comprising the step of heating the tubular shell in the collapsed position along at least the first hinged portion and the second hinged portion to create a material memory and thereby bias the tubular shell in the collapsed position.

13. The method of claim 11 wherein the step of removing material is accomplished with a laser.

14. The method of claim 13 wherein the step of removing material from the wall of the tubular shell comprises perforating the wall of the shell to form a plurality of perforations along the inner arc and the outer arc of the tubular shell.

15. The method of claim 13 wherein the step of removing material from the wall of the tubular shell comprises removing between about 10% and 90% of the wall thickness along said first and second hinged portions.

16. The corneal implant of claim 1 wherein the hollow tubular shell contains a biocompatible material.

17. The corneal implant of claim 16 wherein the biocompatible material is selected from the group consisting of a silicone polymer, a urethane polymer, an acrylic polymer, a polyester, and a fluoropolymer resin.

18. The corneal implant of claim 16 wherein the biocompatible material of the tubular shell has a material memory such that the tubular shell is biased towards a collapsed position.

* * * * *